US009320613B2

(12) United States Patent
Dmuschewsky

(10) Patent No.: US 9,320,613 B2
(45) Date of Patent: Apr. 26, 2016

(54) LATERALLY EXPANDABLE INTERVERTEBRAL FUSION IMPLANT

(71) Applicant: FACET-LINK INC., Rockaway, NJ (US)

(72) Inventor: Klaus Dmuschewsky, Hamburg (DE)

(73) Assignee: Facet-Link Inc., Rockaway, NJ (US)

( * ) Notice: Subject to any disclaimer, the term of this patent is extended or adjusted under 35 U.S.C. 154(b) by 0 days.

(21) Appl. No.: 14/107,597

(22) Filed: Dec. 16, 2013

(65) Prior Publication Data
US 2014/0188224 A1 Jul. 3, 2014

Related U.S. Application Data

(60) Provisional application No. 61/738,278, filed on Dec. 17, 2012.

(30) Foreign Application Priority Data

Dec. 14, 2012 (DE) .......................... 20 2012 011 960

(51) Int. Cl.
*A61F 2/44* (2006.01)
*A61F 2/46* (2006.01)
(Continued)

(52) U.S. Cl.
CPC .............. *A61F 2/4455* (2013.01); *A61F 2/442* (2013.01); *A61F 2/447* (2013.01); *A61F 2/4611* (2013.01);
(Continued)

(58) Field of Classification Search
CPC .......... A61F 2/44; A61F 2/442; A61F 2/4425; A61F 2/4455; A61F 2/4465; A61F 2/447
USPC ............................................ 623/17.16, 17.11
See application file for complete search history.

(56) References Cited

U.S. PATENT DOCUMENTS

2008/0243255 A1* 10/2008 Butler et al. ............... 623/17.16
2009/0157084 A1 6/2009 Aalsma et al.
(Continued)

FOREIGN PATENT DOCUMENTS

WO WO-00/25706 5/2000
WO WO-2007/121320 10/2007
(Continued)

OTHER PUBLICATIONS

European Search Report dated Jun. 5, 2013, directed to EP Application No. 12197580.9; 9 pages.
(Continued)

*Primary Examiner* — Jerry Cumberledge
*Assistant Examiner* — Tessa Matthews
(74) *Attorney, Agent, or Firm* — Morrison & Foerster LLP

(57) ABSTRACT

The invention relates to an intervertebral fusion implant for fusing two adjacent vertebrae, comprising an adjustable support body, the base surface and cover surface of which are configured to bear on end plates of the adjacent vertebrae, wherein provision is made for a side bracket, which can be pivoted laterally about a hinge and the base and cover of which have a planar design, and provision is made for an actuator for pivoting out the side bracket into a position (working position) spread from the support body. As a result, the implant has particularly small dimensions and can, after assembly at the envisaged implantation site, be actuated in such a way that it becomes larger and thereby affords a larger support surface for support in the intervertebral space. Thus, even comparatively large-area defects can be treated by minimally invasive surgery.

25 Claims, 5 Drawing Sheets

(51) Int. Cl.
*A61F 2/28* (2006.01)
*A61F 2/30* (2006.01)

(52) U.S. Cl.
CPC ... *A61F 2002/2835* (2013.01); *A61F 2002/304* (2013.01); *A61F 2002/30019* (2013.01); *A61F 2002/3052* (2013.01); *A61F 2002/3093* (2013.01); *A61F 2002/30112* (2013.01); *A61F 2002/30393* (2013.01); *A61F 2002/30395* (2013.01); *A61F 2002/30401* (2013.01); *A61F 2002/30405* (2013.01); *A61F 2002/30471* (2013.01); *A61F 2002/30484* (2013.01); *A61F 2002/30507* (2013.01); *A61F 2002/30542* (2013.01); *A61F 2002/30553* (2013.01); *A61F 2002/30556* (2013.01); *A61F 2002/30579* (2013.01); *A61F 2002/30624* (2013.01); *A61F 2002/30626* (2013.01); *A61F 2002/30629* (2013.01); *A61F 2002/30632* (2013.01); *A61F 2002/30845* (2013.01); *A61F 2002/4475* (2013.01); *A61F 2002/4624* (2013.01); *A61F 2002/4627* (2013.01); *A61F 2002/4629* (2013.01); *A61F 2002/4635* (2013.01); *A61F 2002/4638* (2013.01)

(56) References Cited

U.S. PATENT DOCUMENTS

| | | | |
|---|---|---|---|
| 2011/0276141 A1* | 11/2011 | Caratsch | 623/17.16 |
| 2012/0123546 A1* | 5/2012 | Medina | 623/17.16 |
| 2012/0197299 A1 | 8/2012 | Fabian, Jr. | |
| 2012/0209386 A1* | 8/2012 | Triplett et al. | 623/17.16 |
| 2012/0259416 A1* | 10/2012 | Blackwell et al. | 623/17.16 |
| 2012/0271422 A1 | 10/2012 | Miller et al. | |
| 2013/0041471 A1* | 2/2013 | Siegal et al. | 623/17.16 |
| 2013/0079883 A1* | 3/2013 | Butler et al. | 623/17.16 |
| 2013/0103156 A1* | 4/2013 | Packer et al. | 623/17.16 |
| 2013/0304214 A1* | 11/2013 | Siegal et al. | 623/17.16 |
| 2013/0325128 A1* | 12/2013 | Perloff et al. | 623/17.16 |

FOREIGN PATENT DOCUMENTS

| | | |
|---|---|---|
| WO | WO-2010/105181 | 9/2010 |
| WO | WO-2012/115631 | 8/2012 |

OTHER PUBLICATIONS

International Search Report and Written Opinion dated Mar. 7, 2014, directed to International Application No. PCT/EP2013/076688; 10 pages.

* cited by examiner

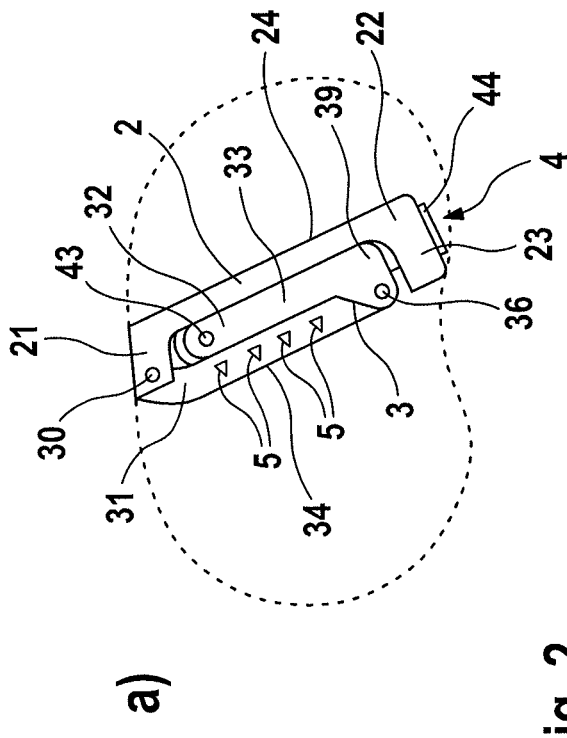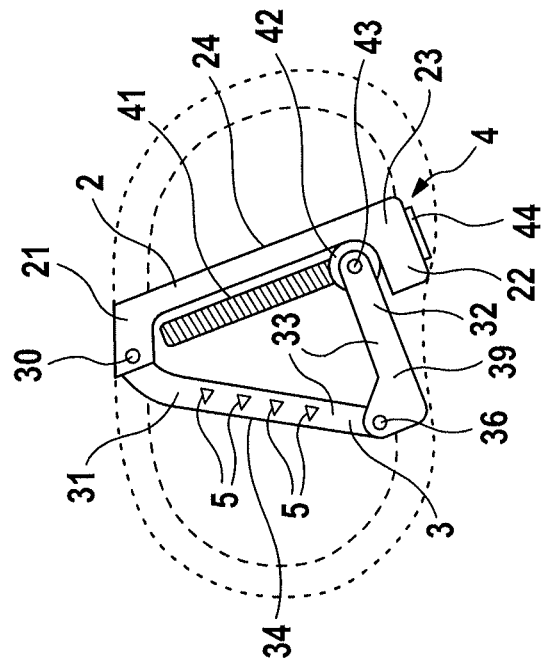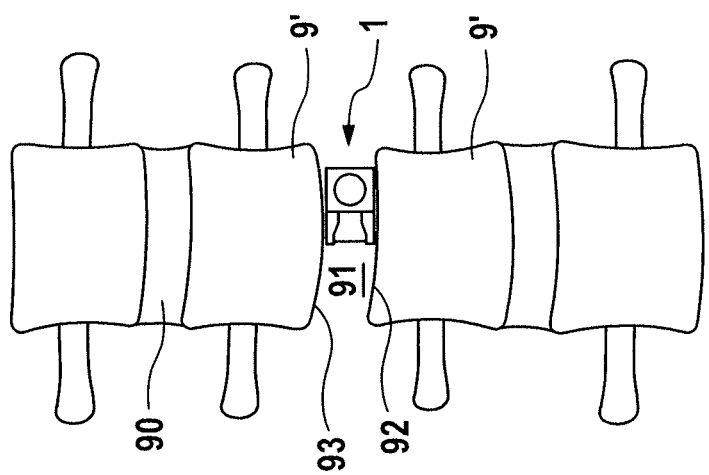
Fig. 2
Fig. 1

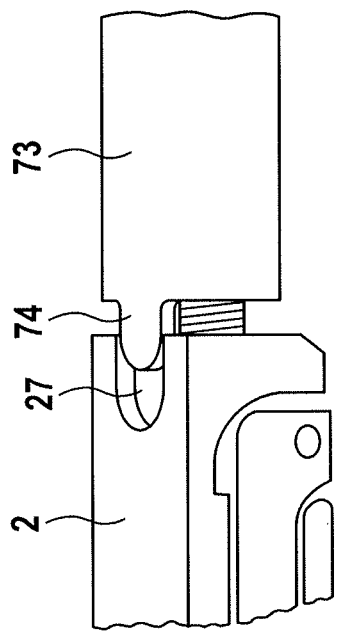
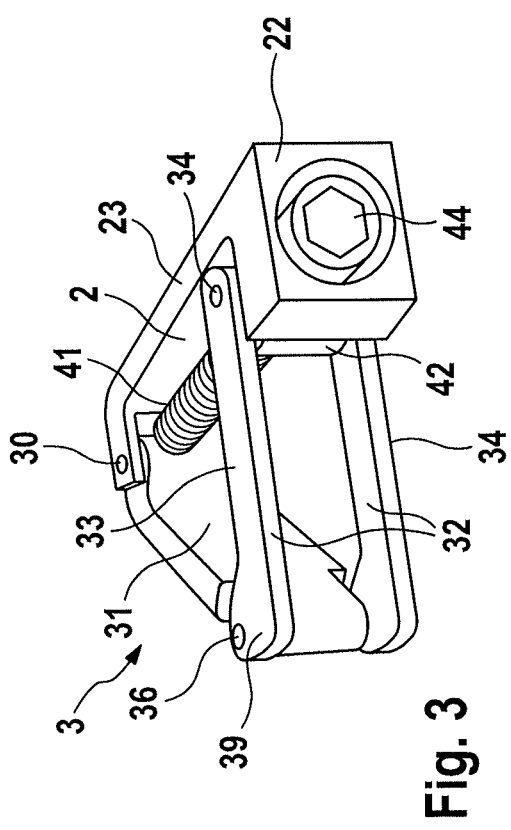
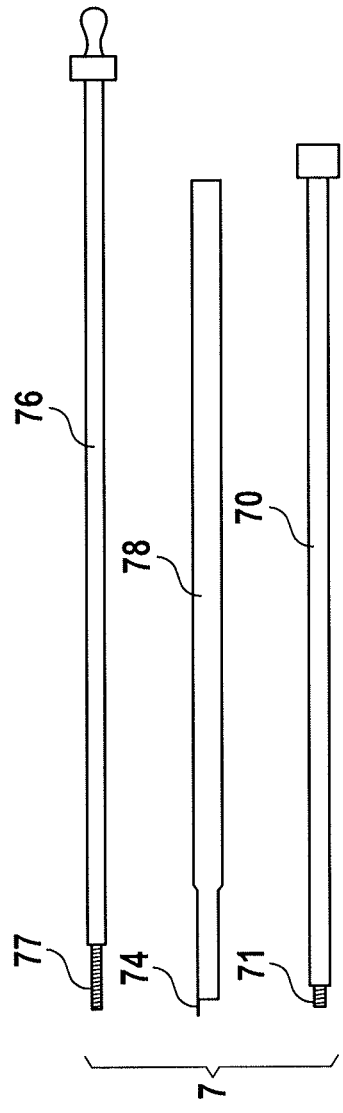

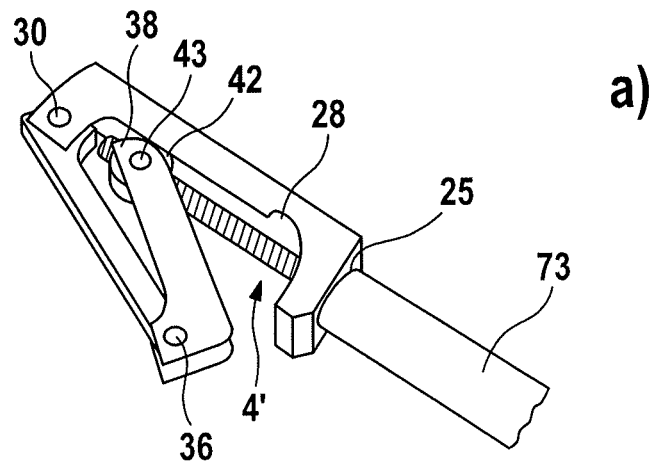
a)
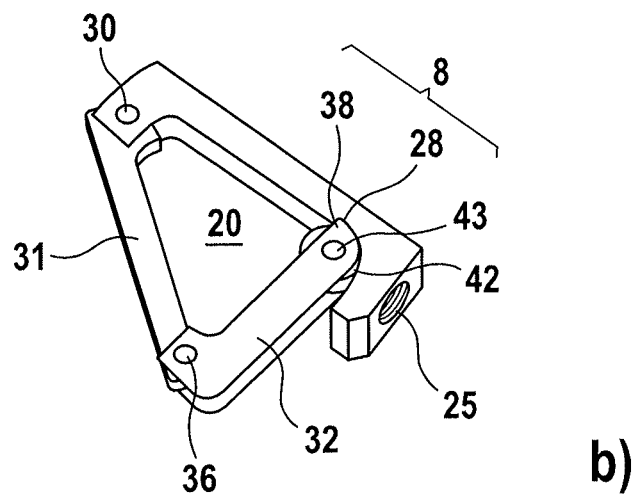
b)
Fig. 8 a)
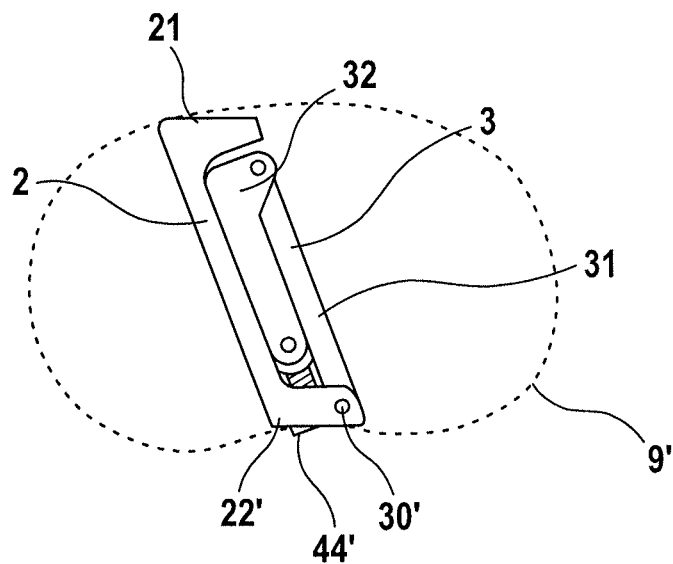
Fig. 9
b)
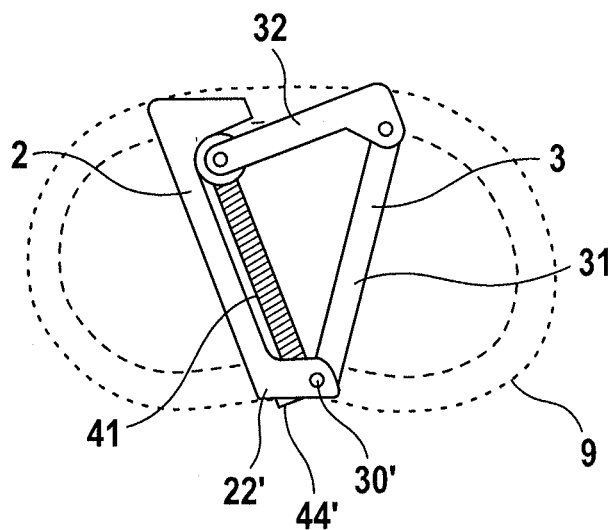

LATERALLY EXPANDABLE INTERVERTEBRAL FUSION IMPLANT

REFERENCE TO RELATED APPLICATIONS

This application is a nonprovisional of U.S. Provisional Application No. 61/738,278, filed Dec. 17, 2012, which claims priority to German Application No. 20 2012 011 960.5, filed Dec. 14, 2012, the entire contents of which are incorporated herein by reference.

FIELD OF THE INVENTION

The invention relates to an intervertebral fusion implant for fusing two adjacent vertebrae, comprising an adjustable support body, the base surface and cover surface of which are configured to bear on the vertebrae.

BACKGROUND OF THE INVENTION

The intervertebral disks of the vertebral column suffer degeneration as a result of wear or of pathological changes. If conservative treatment by medication and/or physiotherapy is ineffective, surgical treatment is sometimes indicated. In this connection, it is known for a movable or immovable implant to be inserted into the intervertebral space containing the degenerated intervertebral disk. This implant takes over the support function of the degenerated intervertebral disk and to this extent restores a stable support between the adjacent vertebrae. Immovable implants are also referred to as "fusion implants".

Various surgical techniques are known for implanting the fusion implants. A traditional surgical technique involves a ventral access route, in order thereby to avoid the danger of damaging the spinal cord in the vertebral column. However, this advantage is obtained at the price of a very long access route through the abdominal cavity or thoracic cavity of the patient. Since this can cause complications, an alternative access route has become established, namely from the dorsal direction. Although the latter affords the advantage of a short route, there is the danger of collision with or damage to the spinal cord. To minimize this danger, the operation is usually performed by minimally invasive surgery. Approaches of this kind directly from the dorsal direction or more from the side are known as PLIF (posterior lumbar intervertebral fusion) or TLIF (transforaminal lumbar interbody fusion), in which the intervertebral disk is exposed from the posterior or lateral direction, respectively. Because of the small transverse incisions used in the approach by minimally invasive surgery, the size of the fusion implants is of course greatly restricted here.

For treatment using the PLIF or TLIF technique, very small fusion implants are known. They afford the advantage of being able to be implanted by minimally invasive surgery thanks to their small size. However, an inherent disadvantage of their small size is that the support function is limited because of the small dimensions and is sometimes inadequate. Although a larger size of the fusion implants would improve the support function, this is impractical because of the limits of minimally invasive surgery.

SUMMARY OF THE INVENTION

The invention has set out to improve a fusion implant of the type mentioned at the outset to the extent that, while still having a small access cross section, as is conventional for minimally invasive surgery, it can nevertheless achieve an improved support effect.

In an intervertebral fusion implant for fusing two adjacent vertebrae, comprising an adjustable support body, the base surface and cover surface of which are configured to bear on end plates of the adjacent vertebrae, provision is made, according to the invention, for a side bracket, which can be pivoted laterally about a hinge and the base and cover of which have a planar extension, and provision is furthermore made for an actuation means for pivoting out the side bracket into a position (working position) spread from the support body.

The invention is based on the concept of developing an intervertebral fusion implant which has particularly small dimensions in an assembly position and can, after the assembly at the envisaged implantation site, be actuated in such a way that it becomes larger and thereby affords a larger support surface for support in the intervertebral space. The latter state is referred to as working position. As a result, the implant according to the invention unifies the advantage of access through a comparatively small access opening, as is typical for minimally invasive surgery, with the advantage of a comparatively large support surface, as is typical for conventional implants implanted in a substantially more invasive fashion.

The invention is based on the concept of, as a result of a lateral pivot mechanism, configuring the implant to be as small as possible for assembly and, by pivoting out, configuring the implant to be as large as possible at the envisaged implantation site. Here the seemingly contradictory goals of, firstly, the small size for implantation and also of the largest possible support surface for fusing the vertebrae to one another are linked. The implant according to the invention is therefore also suitable for treating comparatively large-area defects of an intervertebral disk, to be precise even if the operation is merely to be undertaken by way of minimally invasive surgery. There are no examples of this in the prior art.

The side bracket is expediently configured as a toggle expander, which comprises a pivot arm with a spreader arm. The result of this is an approximately triangular structure, which enables good and safe guidance of the pivoting-out arm, and the risk of jamming during the pivoting, which could lead to blocking of the implant, is effectively counteracted thereby. It is particularly expedient if the spreader arm is locked on the support body in the working position. Such locking ensures that the working position is maintained, even if large loads occur. In a proven embodiment, a sliding piece is attached to the spreader arm and displaced, in particular retracted, by the actuation means during the spreading and it preferably latches into recesses when the working position is reached. The latching results in positive locking, affording particularly high security against undesired detachment.

In order to ensure as small as possible dimensions of the implant during the assembly, the side bracket is preferably retracted into the support body. The smallest possible design is obtained by such positioning. As a result of this, the largest possible size of the support body can be selected; accordingly, the side bracket retracted therein can also be selected to be relatively large.

In order to simplify the insertion and counteract the risk of catching on surrounding tissue, the base and the cover of the side bracket are preferably configured such that they lie flush against the base and/or cover surfaces of the support body in the assembly position. This results in a continuous surface without interspace. It has particularly proven its worth if the base and the cover of the side bracket lie in a plane, i.e. they are aligned with the base and/or cover surface of the support body. What this achieves is that, after spreading, the base and the cover of the side bracket have reliable contact with the end plates of the two adjacent vertebrae, to be precise in the same manner as the support body itself.

In order to promote the implant growing into the intervertebral space, provision can be made for cutting teeth to be arranged on the base surface and/or the cover surface of the support body and/or on the base or cover of the side bracket. The cutting teeth can, particularly during the spreading motion, bring about trimming of the endplate, as a result of which natural bone growth and hence the sought-after fusion of the two vertebrae is promoted and accelerated.

A widening is expediently provided at the free end of the side bracket, to be precise respectively for the base and for the cover. This widening increases the load-bearing surface in the region of the free end of the side bracket. The supporting effect is thereby further improved.

It has proven its worth to design the side bracket to be shorter than what corresponds to the length of the support body. A preferred value lies in the range from 0.7 to 0.9 times the length of the support body. A geometry for the spread state that is very expedient for the practical requirements emerges if the hinge for the side bracket is positioned in such a way that the support body and the side bracket form an approximate isosceles triangle in the spread state. This can achieve a secure support of the end plates, particularly in the regions thereof close to the edge, which are provided with a relatively hard cortical layer. The support effect is then substantially better than in the case of conventional implants, which, due to their small nature, are rather to be positioned in the center of the end plates where the load capacity of the vertebrae is significantly smaller.

The side bracket is preferably configured in such a way that it pivots out at least by a travel corresponding to three times the value of the width of the support body. The result of this is a base width for the implant which enables secure support, even in the case of only a single implant in an intervertebral space.

For the practical application, it is advantageous if an end face, preferably an anterior end face, of the support body is beveled and substantially flat. Here, the anterior end face is understood to be the one which, in the implanted state, points to the frontal side of the patient; accordingly, the posterior side is the one which points in the dorsal direction. By virtue of the end face being flattened, the risk of tissue irritations of the tissue adjoining the vertebral bodies, in particular of the large vessels extending there, is reduced. The risk of injuries as a result of the implantation is significantly reduced thereby.

In order to enable reliable actuation of the intervertebral fusion implant through the same access which is also provided for the implantation of the implant, provision is preferably made for an end-face connector, preferably on a posterior end face, for the actuation means. As a result, the actuation can occur through the same access, without this requiring a change of the access or even the laying of an additional access.

The actuation means expediently has a self-retaining design. What this achieves is that the side bracket is fixed in the pivoted-out position without additional support. An expedient embodiment for the actuation means provides for a spindle as actuator. This enables precise movement true to position since every rotational movement of the spindle achieves a specific defined measure of spreading predetermined by the pitch. Furthermore, the spindle enables reversible actuation such that the spreader arm can optionally also be pivoted back in again if unexpected problems arise during the implantation. The spindle affords the further advantage of being inherently self-retaining.

If the self-retaining property is not to be decisive after spreading has taken place because, for example, the bracket is in any case securely held in its spread position by locking, provision can be made for the spindle to be removable. As a result, it is possible for the spindle to be removed after the implantation is complete. On the one hand, this affords the advantage that material foreign to the body does not necessarily remain and, on the other hand, this affords the advantage of it being possible to introduce bone material, such as grafts or chips, into the cavity in the support body created thus. Bone material introduced thus promotes bone growth and thereby accelerates the fusion of the adjacent vertebral bodies. Provision is preferably made for an opening through which, in the case of an actuation means, there is a clear access to the cavity in the support body. This will often be the opening through which the actuation means was introduced into the support body.

The invention furthermore is furthermore based on the concept of an instrument set for the intervertebral fusion implant, comprising a guide tube, an insertion rod and an actuation rod. The insertion rod is inserted into the guide tube and connected to the intervertebral fusion implant on the posterior end face thereof. For the rotationally secure hold of the implant on the guide tube, the latter preferably has a tongue which is designed for engagement into a corresponding recess in the support body of the intervertebral implant. Finally, the actuation rod is pushed through the guide tube with the insertion rod. It serves for actuating the actuation means. It preferably itself carries part of the actuation means, namely in the form of a thread at the front end thereof, with the thread acting as a spindle for the actuation means.

BRIEF DESCRIPTION OF THE DRAWINGS

The invention will be explained in more detail below with reference to the attached drawing, in which advantageous exemplary embodiments are depicted. In detail:

FIG. 1 shows a schematic view of an intervertebral fusion implant, in the intervertebral space between the vertebral bodies;

FIG. 2 shows illustrations of the exemplary embodiment in accordance with FIG. 1 in assembly position and working position;

FIG. 3 shows a perspective illustration of a first exemplary embodiment;

FIG. 4 shows an illustration of an instrument set;

FIG. 5 shows a detailed illustration in relation to connecting an insertion instrument;

FIG. 8 shows illustrations of the second exemplary embodiment for an intermediate state during the assembly and after completion of the assembly in the working position; and FIG. 9 shows illustrations of a third exemplary embodiment in assembly and working position.

DETAILED DESCRIPTION OF THE INVENTION

Figure 6:
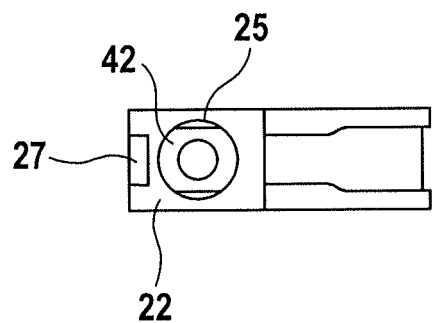
FIG. 6 shows a frontal view of a second exemplary embodiment.
Figure 7:
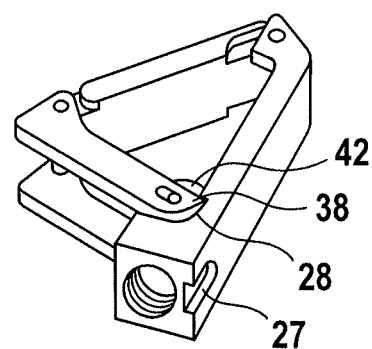
FIG. 7 shows a perspective illustration of a second exemplary embodiment.

An intervertebral fusion implant, denoted by reference sign 1 in its entirety, is provided for implantation in an intervertebral space 91 between two immediately adjacent vertebral bodies 9, 9'. In a physiologically intact vertebral column, an intervertebral disk 90 is located in the intervertebral space between the vertebrae. This intervertebral disk may undergo degeneration as a result of disease or wear, with the result that it has to be at least partially resected. In order to achieve sufficient support of the intervertebral space 91, despite the loss of intervertebral disk material, and to thereby prevent collapse of the vertebral column, the intervertebral fusion implant 1 is inserted into the intervertebral space 91. It provides a supporting action and thus facilitates fusion of the two adjacent vertebrae 9, 9' in a natural way through bone growth.

Reference is now made to the illustration in FIGS. 2 and 3. The first exemplary embodiment depicted there comprises a support body 2 with a side bracket 3 arranged thereon in a pivotable manner by means of a hinge 30. The side bracket has a two-part design with a pivot arm 31, which is mounted movable in a pivoting manner with one end on the hinge 30 and is likewise connected movable in a pivoting manner to a spreader arm 32 by means of a second hinge 36. This results in a structure which can pivot out like a toggle (cf. FIG. 2*b*).

Provision is furthermore made for an actuation means 4, which, in the depicted exemplary embodiment, comprises an integrated actuation spindle 41 and a sliding piece 42. The sliding piece 42 is arranged movable in a pivoting manner on the free end of the spreader arm 32 by means of a holding pin 43. In the center, the sliding piece 42 has a through-hole with a female thread. The spindle 41 of the actuation means is guided therethrough and the former is mounted in a posterior end wall 22 of the support body 2 by means of the head 44 thereof. If the spindle 41 is rotated by rotating the spindle head, the sliding piece 42 moves in the posterior direction, starting from an assembly position (see FIG. 2*a*) at the anterior end of the spindle, wherein the pivot arm 31 and the spreader arm 32 pivot out laterally like a knee joint.

On its anterior, front end face 21, the support body 2 has a flat bevel. The latter has an angle of approximately 20° with respect to a normal of a longitudinal axis of the support body 2 formed by the spindle 41. What this bevel achieves is a flat, non-protruding design of the front end face. The risk of irritation of tissue lying in front of the vertebra is thereby minimized.

The support body 2 has a cover surface 23 on its upper side and, correspondingly, a base surface 24 on its lower side. They serve for bearing on the corresponding end plates 92, 93 of the two adjacent vertebral bodies 9, 9'. Flush on a level therewith is the cover 33 or the base 34 of the side bracket 3. What this achieves is that there is support on the pivoted-out side bracket at the same level as the support from the support body 2. In the assembly position, the cover 33 lies flush on the cover surface 23 of the support body; the same applies accordingly to the base 34 in respect of the base surface 24.

Teeth 5 are arranged on the cover 33 and on the base 34 (not depicted there). The teeth are aligned in such a way that, when the side bracket 3 is pivoted out, they remove bone material from the associated end plate 92, 93 and, as a result, carry out trimming of the bone in this region.

For implantation purposes, provision is made for an instrument set 7, which is depicted in FIG. 4. It comprises an insertion rod 70, a guide tube 73 and an actuation rod 76. The insertion rod is pushed through the guide tube 73 and, with the front end thereof, is attached to the support body 2 of the intervertebral fusion implant 1. The group created thus can be introduced into the intervertebral space 91 through a minimally invasive access, which for example was created within the scope of the PLIF (posterior lumbar intervertebral fusion) method. It then assumes there the position depicted in FIG. 2*a*. In a next step there is spreading by the actuation means. In the depicted exemplary embodiment in accordance with FIGS. 2 and 3, a suitable screw drive is, to this end, inserted into the screwing head 44 of the actuation spindle 41 and the side bracket 3 is thereby pivoted out by rotating the spindle 41. This occurs in such a manner by virtue of the sliding piece 42 being pulled in the posterior direction, i.e. toward the screw head 44, by the spindle 41 being rotated and hence by virtue of the spreader arm 32 attached there pivoting out the side arm 31. Finally, the assembly position depicted in FIG. 2*b* is reached.

In FIG. 2*b*, it is possible to identify that, in particular, the hard cortical edge of the vertebral body, identified by the dashed line, bears on broad surface portions on the cover surface or base surface in a manner expedient for force transmission, namely in the region of the posterior end face and the anterior end face of the support body 2 and on the widening 39 provided on the side bracket 3. Thanks to this broad design, a very good force transmission can be achieved even with a comparatively small implant.

The third exemplary embodiment depicted in FIG. 9 is a variant of the first exemplary embodiment. It differs substantially in that the side bracket 3 is hinged on the posterior end using a hinge 30', and not on the anterior end as in the first embodiment depicted in FIGS. 1 to 3. The intervertebral fusion implant in accordance with the third exemplary embodiment therefore accordingly spreads in an opposite sense, namely in the anterior direction. As a result, a screw head 44' for the actuation spindle 41 is situated on the same side as the hinge 30', which correspondingly has a lateral offset in order to provide sufficient installation space here. Furthermore, the posterior end face 23' is also beveled in this embodiment in order to achieve a termination which is as smooth as possible and does not harbor the risk of irritating surrounding tissue. Otherwise, the same parts have the same functions as in the above-described first exemplary embodiment. They are also provided with the same reference signs. In this respect, reference is made to the description above.

A second exemplary embodiment is explained with reference to FIGS. 5-8. It substantially has the same design as the first exemplary embodiment, with the same or similar elements being denoted by the same reference signs. It differs in terms of the actuation means 4'. Thus, the actuation means 4' provides a sliding piece 42, by means of which spreading of the side bracket 3 is achieved in the same fashion as in the first exemplary embodiment. However, the actuation means 4' does not comprise its own spindle, but merely a corresponding spindle mount in an enlarged opening 25 on the posterior end face 22 of the support body. This enlarged opening 25 can be provided with a female thread. The diameter thereof is approximately twice the size of the through-hole with the thread, leading through the hinge piece.

Furthermore, a U-shaped recess 27 extending from the end face 22 is provided on the base side 24 of the support body 2. It serves for holding a fixation tongue of the instrument set, as will be explained below.

Furthermore, recesses 28 are arranged on the cover and base surfaces 23, 24 in the region of the support body in which the sliding piece 42 is positioned in the working position. These recesses are shaped in such a way that they hold the sliding piece-side end of the spreader arm 32 in an positive locking manner. In this fashion, the spreader arm is locked in the anterior/posterior direction, as a result of which the pivot arm 31 is also locked in its pivoted-out position. In order to ensure secure, positive locking, the hinge piece-side end of the spreader arm 32 is provided with engagement edges 38. The recesses 28 and 38 thus together form a locking means 8.

As a result of the locking means 8 being independent of the actuation means 4, it is no longer necessary for a spindle 41 to remain in the implant after pivoting-out the side bracket 3. Said spindle can therefore be removed. As a result, the opening 25 provided for holding the spindle head 44 becomes unoccupied and can act as access opening to an interior space 20 in the support body 2. As a result, grafts or chips with bone material can be introduced through the minimally invasive access after inserting the implant and spreading it into the working position in order thereby to promote the fusion of the two adjoining vertebral bodies 9, 9'.

In the following text, the implantation is described with reference to the instrument set, as depicted in FIG. 4. The guide tube 73 has a tongue 74 at its front end, which engages in an positive locking manner in the recess 27 in the support body 2 and thus fixes the latter secured against rotation on the guide tube 73. The insertion rod 70 is pushed through the guide tube 73 and the thread 71 thereof at the front end is screwed into the female thread in the opening 25. As a result, the implant at the guide tube 73 is securely held on the insertion rod 70 (see FIG. 5). In the next step the actuation rod 76 is guided through the insertion rod 70 which, for this purpose, has been drilled to be hollow. With its thread 77, the actuation rod 76 engages into the sliding piece 42. As a result, the implant 1' is held on the instrument set in its assembly position, as depicted in FIG. 6. It can then be introduced into the intervertebral space 91 through the minimally invasive access. After this, the sliding piece 42 is moved in the posterior direction by rotating the actuation rod 76, which acts as spindle for the actuation means 4, as a result of which the spreader arm 32 is moved outward and the pivot arm 31 is accordingly pivoted out in the lateral direction. The assembly position with fully pivoted-out pivot arm 31 is reached when the detents 38 of the locking means 8 engage in the recess 28. As a result, the implant is locked. The actuation rod 76 can then be taken out and the guide tube 73 with the insertion pin 70 can likewise be removed.

The invention claimed is:

1. An intervertebral fusion implant for fusing two adjacent vertebrae, comprising
    an adjustable support body, a base surface of which and a cover surface of which are configured to bear on end plates of adjacent vertebrae;
    a side bracket, which can be pivoted laterally about a hinge, and a base of which and a cover of which have a planar design, wherein the side bracket has a length of approximately 0.7 to 0.9 times a length of the support body; and
    an actuator that pivots out the side bracket into a working position spread from the support body,
    wherein the side bracket comprises a toggle expander with a pivot arm and a spreader arm, and a sliding piece is attached to the spreader arm and displaced by the actuator.

2. The intervertebral fusion implant of claim 1, wherein the spreader arm locks in the working position.

3. The intervertebral fusion implant of claim 1, wherein the side bracket retracts into the support body in an assembly position.

4. The intervertebral fusion implant of claim 3, wherein one or both of the base and cover of the side bracket lie adjacent to one or both of the base and cover surfaces of the support body in the assembly position.

5. The intervertebral fusion implant of claim 1, wherein one or both of the base and cover of the side bracket lie in the same plane with one or both of the base and cover surfaces of the support body.

6. The intervertebral fusion implant of claim 5, wherein cutting teeth are arranged on one or both of the base and cover.

7. The intervertebral fusion implant of claim 1, wherein a free end of one of more of the base and cover is wider than an opposite end of one or more of the base and cover.

8. The intervertebral fusion implant of claim 1, wherein the hinge for the side bracket is positioned such that the support body and the side bracket form an approximate isosceles triangle when in the working position.

9. The intervertebral fusion implant of claim 1, wherein the side bracket pivots out at least by a distance of three times the width of the support body.

10. The intervertebral fusion implant of claim 1, wherein an end face of the support body is beveled and substantially flat.

11. The intervertebral fusion implant of claim 10, wherein the end face is an anterior end face.

12. The intervertebral fusion implant of claim 1, wherein an end face comprises a connector for the actuator.

13. The intervertebral fusion implant of claim 12, wherein the end face is a posterior end face.

14. The intervertebral fusion implant of claim 1, wherein the actuator is self-retaining.

15. The intervertebral fusion implant of claim 1, wherein the actuator comprises a spindle.

16. The intervertebral fusion implant of claim 15, wherein the spindle is removable.

17. The intervertebral fusion implant of claim 1, further comprising an opening through which, when the actuator is removed, there is a clear access to a cavity in the support body.

18. The intervertebral fusion implant of claim 1, further comprising an attachment for an insertion rod arranged on the support body.

19. The intervertebral fusion implant of claim 18, wherein the attachment is an opening with a female thread.

20. The intervertebral fusion implant of claim 1, further comprising a coupling for a torque support arranged on the support body.

21. The intervertebral fusion implant of claim 1, further comprising a recess on the support body and an engagement edge on the side bracket.

22. An instrument set comprising the intervertebral fusion implant of claim 1, wherein the instrument set comprises a guide tube, an insertion rod, and an actuation rod.

23. The instrument set of claim 22, further comprising a tongue for engagement into the support body of the intervertebral fusion implant arranged at a front end of the guide tube.

24. The instrument set of claim 22, wherein the actuation rod has a thread at a front end thereof, which acts as a spindle for the actuator.

25. The intervertebral fusion implant of claim 1, wherein the sliding piece latches into recesses when the working position is reached.

* * * * *